US00PP14472P39

(12) United States Plant Patent
Pieters

(10) Patent No.: US PP14,472 P3
(45) Date of Patent: Jan. 20, 2004

(54) CHRYSANTHEMUM PLANT NAMED 'GEDI TWO CAM'

(50) Latin Name: *Chrysanthemum morifolium*
Varietal Denomination: Gedi Two Cam

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/138,116

(22) Filed: May 1, 2002

(65) Prior Publication Data

US 2003/0208822 P1 Nov. 6, 2003

(51) Int. Cl.[7] ..... A01H 5/00
(52) U.S. Cl. ..... Plt./293

(58) Field of Search ..... Plt./293, 287, 292, Plt./298

(56) References Cited

U.S. PATENT DOCUMENTS

PP10,213 P 1/1998 Wain ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 42 days of short day length, free branching habit, red ray florets, very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Cam.'

BACKGROUND OF THE INVENTION

The new cultivar is a product of hybridization of a female parent, cultivar 'Preco' (undistributed in the United States), and a male parent, 'Red Urano' (U.S. Plant patent application Ser. No. 09/550,156, now abandoned). This cultivar was discovered and selected by the inventor in October 1997.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Cam' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Cam.' These characteristics in combination distinguish 'Gedi Two Cam' as a new and distinct Chrysanthemum cultivar:

1. Decorative-type inflorescence,
2. Consistent flowering response to short days, blooming consistently after 42 days of short day length,
3. Free branching habit, 4. Red ray florets,
5. Very uniform round growth habit, and
6. Large quantity of blooms per flowering branch.

Plants of the new cultivar are similar to plants of the parent cultivar, 'Preco' in most horticultural characteristics, however plants of the new cultivar differed from plants of the cultivar 'Preco' primarily in ray floret color. The new cultivar 'Gedi Two Cam' induces and develops blooms earlier than the male parent cultivar 'Red Urano' and has fewer ray florets per inflorescence than the male parent. The new cultivar also has an inflorescence which remains decorative.

In comparison to the commercially available variety 'Jenny Wren' (U.S. Plant Pat. No. 10,213), 'Gedi Two Cam' naturally blooms one week earlier and has fewer ray florets. The new cultivar has a deep red inflorescence and more blooms per flowering branch than 'Jenny Wren.'

BRIEF DESCRIPTION OF THE PHOTOGRAPH

The photograph shows a plant of 'Gedi Two Cam' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 146 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Cam'.
Commercial classification: Garden-type Chrysanthemum.
Parentage: Hybridization of a female parent, cultivar 'Preco' (undistributed in the United States), and a male parent, 'Red Urano' (U.S. Plant patent application Ser. No. 09/550,156, now abandoned).

PROPAGATION

Time to rooting: 7 to 14 days at approximately 21° C.
Root description: Fine, fibrous.

PLANT

Growth habit: Mounding herbaceous perennial.
Height: Approximately 20 cm.
Spread: Approximately 26 cm.
Growth rate: Moderate.
Branching characteristics: Free Branching.
Length of lateral branches: Approximately 19 cm.
Number of leaves per lateral branch: Approximately 12.

FOLIAGE

Leaf:
- *Arrangement.*—Alternate.
- *Average length.*—Approximately 6.0 cm.
- *Average width.*—Approximately 4.2 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138A. Mature foliage upper side: Near 139A. Mature foliage under side: Near 138A. Venation upper side: Near 138B. Venation under side: Near 138B.
- *Venation type.*—Palmately net.

Petiole:
- *Average length.*—Approximately 2.5 cm.
- *Color.*—Near 139A.
- *Diameter.*—Approximately 0.3 cm.

BLOOM

Inflorescence:
- *Flowering habit.*—Induced by darkness period greater than 13.5 hours, approximately 42 days of appropriate day length required to induce and develop blooms.
- *Inflorescence form.*—Decorative.
- *Natural flowering season.*—Approximately from the last week of August through the first week of September.
- *Number of inflorescences per lateral branch.*—Approximately 13.
- *Inflorescence diameter.*—Approximately 4.8 cm.
- *Inflorescence depth.*—1.5 cm.
- *Inflorescence longevity on plant.*—Approximately 25 days.
- *Persistence.*—Persistent.

Ray florets:
- *Appearance.*—Matte.
- *Texture.*—Smooth.
- *Average number per flower.*—135.
- *Shape.*—Oblong.
- *Aspect.*—Flat.
- *Margin.*—Entire.
- *Apex.*—Retuse.
- *Length.*—Approximately 2.4 cm.
- *Width.*—Approximately 0.6 cm.
- *Color.*—Upper surface at first opening: Near 46A. Upper surface at maturity: Near 46A. Upper surface at fading: Near 181A. Under surface at first opening: Near 180A. Under surface at maturity: Near 182B. Under surface at fading: Near 182C.

Disc florets:
- *Appearance.*—Shiny.
- *Texture.*—Smooth.
- *Average number per flower.*—Approximately 10.
- *Shape.*—Cylindric.
- *Apex.*—Obtuse.
- *Average length.*—Approximately 0.3 cm.
- *Average width.*—Approximately 0.1 cm.
- *Color: At first opening: Near* 13B. At maturity: Near 21B. At fading: Near 21B.

Peduncle:
- *Length.*—At terminal end (shortest): Approximately 3 cm. At lateral end (longest): Approximately 5.2 cm.
- *Angle to stem.*—Acute.
- *Strength.*—Moderate.
- *Color.*—Near 138A.
- *Habit.*—Upright.
- *Diameter.*—Approximately 0.2 cm.
- *Surface texture.*—Lightly pubescent.

Inflorescence bud:
- *Length.*—Approximately 0.8 cm.
- *Diameter.*—Approximately 1.0 cm.
- *Form.*—Globular.
- *Color.*—Near 138A.

Involucral bracts (phyllaries):
- *Appearance.*—Matte.
- *Texture.*—Lightly pubescent.
- *Number.*—Approximately 115 arranged throughout the entire inflorescence.
- *Shape.*—Oblanceolate.
- *Margin.*—Entire.
- *Apex.*—Acute.
- *Length.*—Approximately 0.8 cm.
- *Width.*—Approximately 0.2 cm.
- *Color.*—Upper side: Near 141B. Under side: Near 141B.

REPRODUCTIVE ORGANS

Ray florets:
- *Number of pistils per flower.*—1.
- *Stigma shape.*—2 branched.
- *Stigma color. Near* 5A.
- *Style color.*—Near 154D.
- *Style length.*—Approximately 0.2 cm.
- *Stamens.*—Absent.

Disc florets (hermaphroditic):
- *Number of pistils per flower.*—1.
- *Stigma shape.*—Two-branched.
- *Stigma color.*—Near 21B.
- *Style length.*—Approximately 0.3 cm.
- *Style color.*—Near 154D.
- *Number of stamens per flower.*—5.
- *Anther shape.*—Tubular.
- *Anther color.*—Near 13A.
- *Pollen color.*—Near 16B.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Cam' as herein illustrated and described.

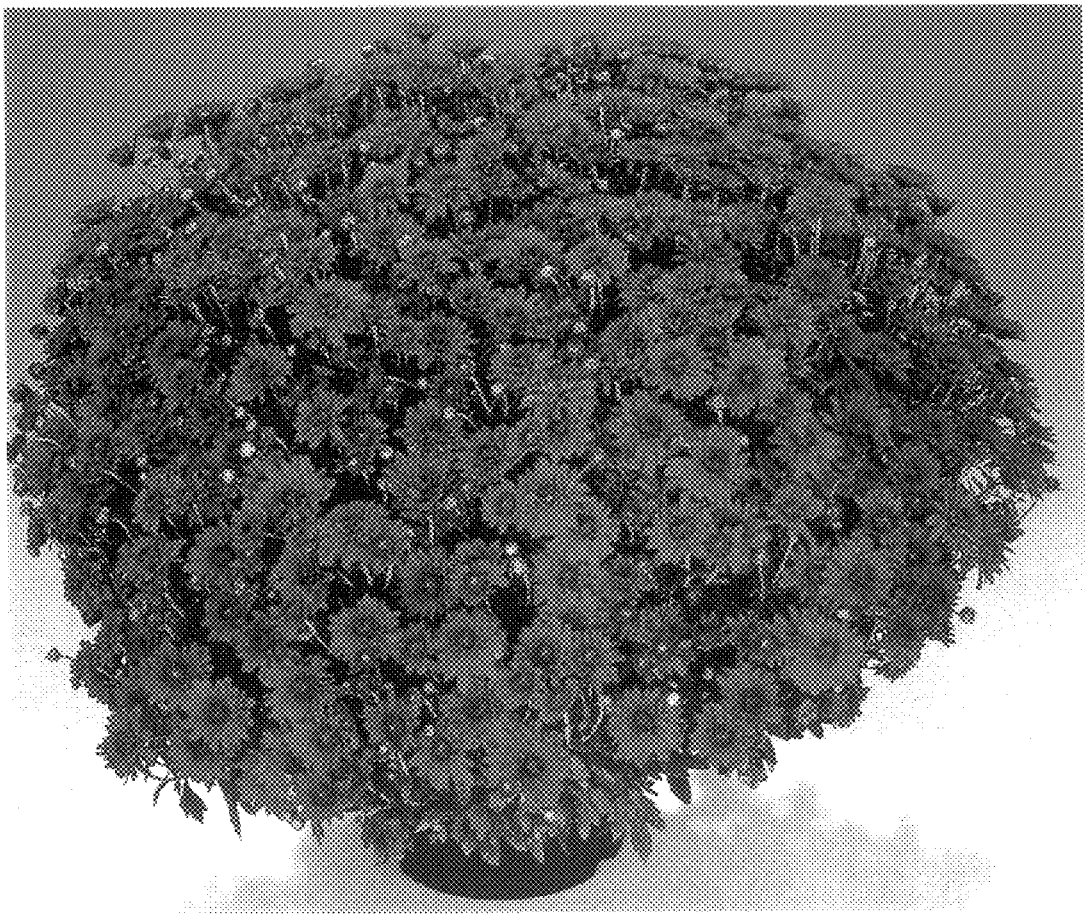

* * * * *